United States Patent
Rinn

(10) Patent No.: US 9,395,316 B2
(45) Date of Patent: Jul. 19, 2016

(54) METHOD AND APPARATUS FOR TESTING OF MATERIALS

(71) Applicant: Frank Rinn, Heidelberg (DE)

(72) Inventor: Frank Rinn, Heidelberg (DE)

( * ) Notice: Subject to any disclaimer, the term of this patent is extended or adjusted under 35 U.S.C. 154(b) by 437 days.

(21) Appl. No.: 13/763,290

(22) Filed: Feb. 8, 2013

(65) Prior Publication Data

US 2013/0241580 A1 Sep. 19, 2013

(30) Foreign Application Priority Data

Feb. 9, 2012 (DE) .......................... 10 2012 002 397

(51) Int. Cl.
*G01R 27/08* (2006.01)
*G01N 27/04* (2006.01)
*G01N 3/40* (2006.01)
*G01N 33/46* (2006.01)

(52) U.S. Cl.
CPC ................ *G01N 27/045* (2013.01); *G01N 3/40* (2013.01); *G01N 27/041* (2013.01); *G01N 33/46* (2013.01); *G01N 2203/0053* (2013.01)

(58) Field of Classification Search
CPC ................. G01R 27/04; G01R 31/343; G01R 2203/0405; G01R 31/34
USPC ......... 324/600, 685–693, 705–713, 415, 421, 324/525, 500
See application file for complete search history.

(56) References Cited

U.S. PATENT DOCUMENTS

| 4,194,031 | A | * | 3/1980 | Cullum .......................... 427/289 |
| 5,621,172 | A | * | 4/1997 | Wilson et al. .................... 73/579 |
| 8,636,748 | B2 | * | 1/2014 | Herndon ......................... 606/131 |

* cited by examiner

*Primary Examiner* — Melissa Koval
*Assistant Examiner* — Trung Nguyen
(74) *Attorney, Agent, or Firm* — Moore & Van Allen PLLC

(57) ABSTRACT

A method and a device for material testing, in particular on trees and timbers, is characterized in that a measurement and preferable recording (storage) of the mechanical penetration resistance of at least two motor (2)-driven, rotating drilling tools (1) penetrating simultaneously into the material beside each other is combined with the measurement and preferable recording of the electrical resistance between just these tools (1).

20 Claims, 1 Drawing Sheet

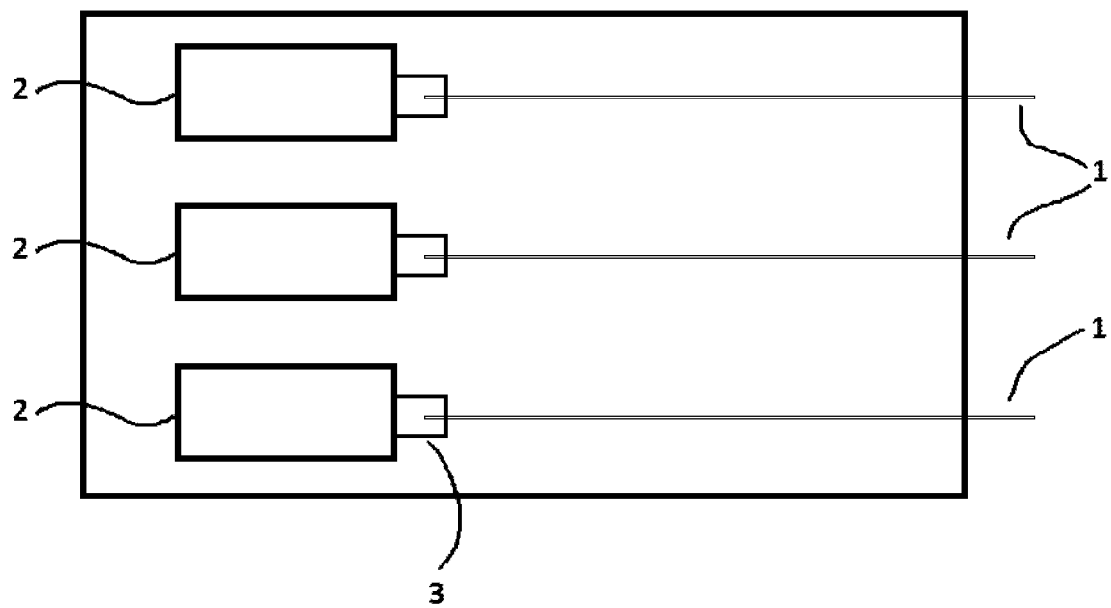

METHOD AND APPARATUS FOR TESTING OF MATERIALS

FIELD OF THE INVENTION

The field of the invention pertains to a method and device for material testing.

BACKGROUND OF THE INVENTION

The penetration resistance to rotating drill bits, measured, for example, via the power consumption of the driving electric motor with a known, preferably linear, characteristic curve, correlates with the density of the drilled material, provided that the geometry of the bit also satisfies specific conditions (inter alia, the tool tip is wider than the shank). This measurement principle has been applied since 1986 to wood, plastics, soils, sandstone and other materials. The drilling resistance profile achieved in this way generally contains information about the state of the material, from which conclusions can be drawn about its stability and loadbearing capacity and also about further properties (in the case of trees, about the annual ring growth, for example). Because of the normally a few millimeters thick bit, the significance is restricted to the local area, so that further measurements often have to be made at a certain spacing. At the bottoms of wooden masts and the tops of floor beams, for example, two measurements are usually made at a spacing of a few centimeters beside each other, in order to be able to detect internal damage with high reliability.

While the presence and extent of damage along the drilling distance can therefore as a rule be detected quite reliably, statements about possible adjacent damage and about the causes of damage are barely possible. The latter is in turn examined in many materials, in particular in biological ones like wood, via a measurement of the electrical conductivity, since the electrical conductivity depends on moisture content, the occurrence of fungus and on other contained substances, which can indicate the causes of damage.

The electrical conductivity, for example in wood, has been measured for decades by two electrically conductive pins being inserted and the electrical resistance between them being measured. It is influenced by water content and substances contained in the wood and by any fungus that may be present or other organisms that degrade wood which, inter alia, increase the number of ions in the wood.

From the combined, optional application of drilling resistance and conductivity measurements, in many cases conclusions can be drawn better as to the causes of damage that has been determined and is to be expected. However, this combination is also subject to some restrictions.

The penetration depth of drilling resistance measuring methods in trees and timbers reaches beyond 1 meter. The pins of electrical conductivity measurements, on the other hand, normally reach only a few to several centimeters. Therefore, the internal areas that are important to damage analysis, for example about 20 cm below soil level at the bottom of wooden masts, generally cannot be reached with the electrical resistance measurement. Although the known electrotomography of trees, the subject of a patent application in 1999 in combination with sound tomography, reaches greater penetration depths, in the case of installed timber is difficult to apply on account of the timbers seldom being accessible all around (similar to the case in wooden masts). In addition, the drying and shrinkage cracks that normally occur there massively restrict the significance.

Since the electrical conductivity likewise depends on the water content and on the presence of anions and cations, for example resulting from fungal infection, it is not possible to conclude from the conductivity values on their own that damaging degradation of wood is taking place. Therefore, the combination with the drilling resistance measurement is expedient since, given an appropriately good and linear technical resolution, it shows whether timber has already been degraded. However, such types of damage can be determined in this way only when timber degradation worth mentioning has occurred. To this extent, there can be combinations in which, even via a combination of drilling resistance measurement and electrical conductivity measurement, no clear statements about early stages of pathological fungal infection are possible (in particular not at greater drilling depths).

In addition, there are cases of a naturally increased but not pathogenic water content and non-damaging fungal infection—although both increase the conductivity appropriately considerably, there is no risk to the tree. Therefore, following conductivity measurements on the tree, erroneous assessments and felling often occurred, which in retrospect proved to be unnecessary.

However, with the water content, the thermal conductivity of the wood also increases in addition to the electrical conductivity. The measurement thereof therefore permits differentiation as to whether an increased electrical conductivity is brought about only by an increased water content or else by pathological infection. In the case of pathological infection, the electrical conductivity rises substantially more highly than only as a result of increased moisture.

An optionally combined application of the methods described here has barely been carried out hitherto for reasons of expenditure, time and costs and, on account of the given application restrictions in the case of the previously available technical devices (e.g. the low penetration depth of the electrical and thermal measurements), would provide no important progress corresponding to the effort.

For the most error-free detection even of early stages of damage deep in the interior of trees and timbers, including wooden masts, there is therefore a need for a combination of the positive properties of the previously separate methods described here and overcoming their restrictions.

SUMMARY OF THE INVENTION

Embodiments of the invention are directed to methods and devices for material testing. In one embodiment, the invention comprises a method for material testing, in particular on trees and timbers, characterized in that a measurement and preferable recording (storage) of the mechanical penetration resistance of at least two motor-driven, rotating drilling tools penetrating simultaneously into the material beside each other is combined with the measurement and preferable recording of the electrical resistance between just these tools. In another embodiment, the method is characterized in that in addition a measurement and preferable recording of the temperature of the tools is made and combined with the measurements of the penetration resistance and electrical resistance. In another embodiment, the method is characterized in that the rotation of the drilling tools is stopped during withdrawal for the purpose of non-disrupted measurement of the electrical conductivity. In another embodiment, the method is characterized in that a rotation and/or feeding of the drilling tools is optionally interrupted from time to time in order to measure the electrical conductivity. In another embodiment, the method is characterized in that the temperature of the tools before, during and after the drilling is measured and recorded.

In yet another embodiment, the method is characterized in that the rise and the fall in the temperature of the drilling tools before, during and after the drilling is measured, recorded and analyzed. In still another embodiment, the method is characterized in that a temperature pulse is introduced into at least one of the drilling tools and the arrival thereof in the other tools is determined by temperature monitoring and is measured and recorded both over time and with respect to intensity.

In one embodiment, the invention comprises a device for carrying out the method according to preceding paragraph. In another embodiment, the device is characterized in that the drilling tools are designed in such a way that only their tip is electrically conductive and thus the measured and recorded electrical resistance over the respectively currently known penetration depth of the tools at the time of the measurement can be assigned to the corresponding area of the material examined respectively located between the drilling tool tips. In another embodiment, the device is characterized in that the measurement of the temperature of the drilling tools is made without contact at the rear end thereof. In another embodiment, the device is characterized in that the drill chuck is optionally connected in a thermally and/or electrically insulated manner to the drive shaft of the motor. In yet another embodiment, the device is characterized in that the drilling tools are not arranged in parallel but at an angle, so that they are, for example, at right angles to the surface of a round specimen (e.g., wooden mast), wherein the measured electrical resistance values are then converted in accordance with the continuously changing spacing between the drilling tools.

BRIEF DESCRIPTION OF THE DRAWING

The single FIG. 1 shows an exemplary embodiment of a device according to the invention with three drilling tools 1 each having drill bits, which are driven by motors 2 and are arranged in a drill chuck 3.

DETAILED DESCRIPTION OF THE INVENTION

The invention now described here describes a new combined method for state detection in ONE measuring operation with ONE device, wherein, on account of specific properties of this combination, the individual measurements have to be carried out in a novel way in order on the one hand to permit a simultaneous combined measurement and on the other hand to achieve reproducible and meaningful results.

The novel method described here according to the invention is firstly based on the measurement of the mechanical penetration resistance of at least two penetrating drilling tools (e.g. drills or drill bits), preferably parallel to each other, wherein, at the same time during the penetration and/or withdrawal, not only the mechanical resistance but also the electrical and thermal conductivity is measured by means of the same drilling probes and recorded.

In order to achieve a higher local resolution of the conductivity values in the drilling direction, the drilling tools can be designed in such a way that only their tip is electrically conductive, for example with a non-conductively coated shank, in particular using Teflon, which at the same time has the advantage of a lower shank friction of the drilling tool. Therefore, the electrical resistance between the electrically conductive tips can be assigned to their respective position in the material examined and the connecting line extending correspondingly therebetween.

In a preferred design variant, the drill bit is therefore non-conductively coated apart from the section in the fixing drill chuck and on the front-side cutter.

In this case, it should be noted that, during the drilling operation, in particular the geometry of the drilling tool head and the ratio of rotational speed to feed rate not only influences the mechanical penetration resistance but also the measured conductivity values.

In this sense, a bit tip with approximately twice the external diameter as compared with the shank, for example 3 to 1.5 mm, which is electrically conductive over about the front 10 mm, tool rotational speeds when drilling in the range between 3000 and 15,000 revolutions per minute, depending on the type of wood, at feed rates of a few to several centimeters per second have proven worthwhile.

The influence of these drilling parameters on the measured values achieved has to be taken into account by means of correction factors in the method calibration. Since the natural bulk density, depending on the type of wood and wood moisture, lies between about 100 and 1400 $kg/m^3$, the drilling and measuring parameters must be capable of adjustment or adaptation within correspondingly wide ranges.

In order to increase the precision of the conductivity measurements, the tool can remain stationary at the relevant positions for a steady-state measurement and, as required, is then drawn back either continuously without rotation or stepwise in order to be able to carry out the conductivity measurement more precisely at defined reference points.

Alternatively, the feeding and rotation of the tool can also be carried out by means of stepping motors which are programmed in such a way that, following each step, they stop for a short time period, in which the conductivity measurements are then made.

Since the optimal spacing between the two drilling lines can differ, depending on the object and material to be examined, the drilling axes can be arranged with a variable spacing, which once more has to be taken into account in the calibration of the conductivity measurements. Typically, 5, occasionally up to 10, centimeters spacing between the axes has proven to be worthwhile; wherein in the case of round objects, such as wooden masts, for example, an optionally variable angular setting proves to be useful, in order to be able to drill in on two axes each at right angles to the surface. The following continuously changing spacing of the drilling axes must be taken into account appropriately when converting the conductivity values.

A variation of the amplitude and frequency of the applied electrical voltage expands the significance of the method and an improved differentiation between different causes which can lead to a higher conductivity. Depending on the nature and stage of a pathogenic fungal infection, the electrical conductivities are changed in a frequency-specific way and once more differently than as a result of an increased water content.

In order, for example, also to be able to differentiate early stages of wood degradation from non-damaging fungal infection and high wood moisture, in an optional embodiment of the device a measurement of the thermal conductivity of the material is additionally made. It increases with the moisture content but barely as a result of fungal infection. Both the (in particular density-dependent) heating of the drilling tools during the drilling and the cooling thereof are measured by the drill and recorded. The higher the water content of the material, the less the drill bit heats up (and the more quickly it cools down, for example when it is at the point of maximum penetration depth). Rotational speed and feed rate of the tool always have to be included in the calculation. Likewise, the values of the electrical conductivity have to be converted in accordance with the thermal conductivity, since the latter permits a statement about the water content and this in turn influences the electrical conductivity.

The temperature measurement can be carried out on drilling tools made of steel, optically and without contact, shortly before the entry point, for example in the guiding drill nose at the top of the drill, but alternatively also in the drill chuck, where contact points necessary for the electrical conductivity measurement are also located in any case.

In an optional embodiment, in order to increase the significance of the thermal measurement, a heat pulse can be transmitted into one of the drilling tools or into several drilling tools and the decay or arrival thereof can be measured in the others. These types of temperature measurements have already been carried out for years using thin needles on trees, in order to monitor the sap flow transport, for example, but until now just not at greater depths.

While the measurement of the heating during and the cooling after the drilling operation, permits a statement about the moisture content of the material, in particular around the drilling channel, to be made, the measurement of the transmission of a heat pulse from one to the other drilling tool supplies information about the state of the material between the relevant drilling axes, where electrical conductivity is also influenced. Therefore, the measured values of the electrical conductivity can be interpreted better, which are likewise intended to permit a statement about the state of the material between the drilling tools.

In this way, restrictions on methods previously used individually are lifted and, by means of a combination, a far more meaningful database is created, which enables more unequivocal and reliable state estimations and assessments of causes. If, for example, the variation in the drilling resistance is normal but the electrical conductivity is increased, an increased thermal conductivity documents the fact that a high moisture content is causative. In the case of low thermal conductivity, in this case a dry, former fungal infection is in turn involved. Therefore, an erroneous assessment can be prevented and complicated and damaging sampling with subsequent laboratory analysis can be avoided.

According to a preferred embodiment of the invention, so to speak a multi-axis electro-thermo drilling resistance measuring method for material testing is realized.

The invention claimed is:

1. A method for destructive material testing, in particular on trees and timbers, the method comprising:
   penetrating the material with at least two motor-driven, rotating drilling tools, the at least two motor-driven, rotating drilling tools being inserted into the material simultaneously beside each other;
   measuring the mechanical penetration resistance of the at least two motor-driven, rotating drilling tools;
   measuring the electrical resistance between the at least two motor-driven, rotating drilling tools used to measure the mechanical penetration resistance; and
   determining the state of the material based upon the measured mechanical penetration resistance and the measured electrical resistance.

2. A method according to claim 1, further comprising recording the measured mechanical penetration resistance and/or the measured electrical resistance.

3. A method according to claim 1, further comprising:
   measuring the temperature of the at least two motor-driven, rotating drilling tools used to measure the mechanical penetration resistance; and
   wherein the determining step comprising determining the state of the material based upon the measured mechanical penetration resistance, the measured electrical resistance and the measured temperature.

4. A method according to claim 1, further comprising recording the measured temperature.

5. A method according to claim 1, further comprising stopping the rotation of the drilling tools during withdrawal for the purpose of non-disrupted measurement of the electrical conductivity.

6. A method according to claim 1, interrupting the rotation and/or feeding of the drilling tools from time to time in order to measure the electrical conductivity.

7. A method according to claim 1, measuring the temperature of the tools before, during and/or after the drilling.

8. A method according to claim 1, further comprising recording the measured temperature of the at least two motor-driven, rotating drilling tools.

9. A method according to claim 1, measuring the rise and the fall in the temperature of the at least two motor-driven, rotating drilling tools before, during and/or after the drilling.

10. A method according to claim 9, further comprising recording the measured temperature of the at least two motor-driven, rotating drilling tools.

11. A method according to claim 9, further comprising analyzing the measured temperature of the at least two motor-driven, rotating drilling tools.

12. A method according to claim 1, further comprising:
    introducing a temperature pulse into at least one of the at least two motor-driven, rotating drilling tools; and
    determining the arrival of the temperature pulse in the other of the at least two motor-driven, rotating drilling tools by temperature monitoring.

13. A method according to claim 12, further comprising measuring the temperature pulse in the other of the at least two motor-driven, rotating drilling tools both over time and with respect to intensity.

14. A method according to claim 12, further comprising recording the temperature pulse in the other of the at least two motor-driven, rotating drilling tools both over time and with respect to intensity.

15. A device for carrying out a method according to claim 1.

16. A device for destructive material testing, in particular on trees and timbers, the device comprising:
    at least two motor-driven, rotating drilling tools for penetrating the material, the at least two motor-driven, rotating drilling tools configured to be inserted into the material simultaneously beside each other, the at least two motor-driven, rotating drilling tools being configured to measure the mechanical penetration resistance of the at least two motor-driven, rotating drilling tools, the at least two motor-driven, rotating drilling tools being further configured to measure the electrical resistance between the at least two motor-driven, rotating drilling tools used to measure the mechanical penetration resistance.

17. A device according to claim 16, wherein each of the at least two motor-driven, rotating drilling tools comprises a tip, wherein only the tips are electrically conductive such that the measured electrical resistance at the currently known penetration depth of the at least two motor-driven, rotating drilling tools at the time of the measurement can be assigned to the corresponding area of the material located between the tips at the time of the measurement.

18. A device according to claim 16, wherein the at least two motor-driven, rotating drilling tools are configured to measure the temperature of the drilling tools, wherein the temperature is measured without contact at the rear end thereof.

19. A device according to claim 16, wherein the at least two motor-driven, rotating drilling tools further comprise:
- a drill chuck;
- a motor;
- a drive shaft connecting the motor to the drill chuck; and
- wherein the drill chuck is optionally connected in a thermally and/or electrically insulated manner to the drive shaft.

20. A device according to claim 16, the at least two motor-driven, rotating drilling tools are not arranged in parallel but the direction of penetration of the drilling tools into the specimen is at an angle to one another, wherein the measured electrical resistance values are then converted in accordance with the continuously changing spacing between the drilling tools.

* * * * *